United States Patent
Gooch et al.

(10) Patent No.: US 7,427,409 B2
(45) Date of Patent: Sep. 23, 2008

(54) BROAD SPECTRUM ANTIMICROBIAL PURIFICATION MATERIALS AND METHODS FOR PURIFYING FLUIDS

(75) Inventors: Jan W. Gooch, Atlanta, GA (US);
Arthur W. Johnston, Atlanta, GA (US);
Arthur F. Johnston, Atlanta, GA (US)

(73) Assignee: Water Visions International, Inc., Atlanta, GA (US)

(*) Notice: Subject to any disclaimer, the term of this patent is extended or adjusted under 35 U.S.C. 154(b) by 0 days.

(21) Appl. No.: 11/539,422

(22) Filed: Oct. 6, 2006

(65) Prior Publication Data

US 2008/0026025 A1 Jan. 31, 2008

Related U.S. Application Data

(60) Provisional application No. 60/820,437, filed on Jul. 26, 2006.

(51) Int. Cl.
*A01N 25/00* (2006.01)
*A01N 25/34* (2006.01)
*A01N 25/32* (2006.01)
*A61K 9/00* (2006.01)

(52) U.S. Cl. .................. 424/405; 424/400; 424/404; 424/406

(58) Field of Classification Search .............. None
See application file for complete search history.

(56) References Cited

U.S. PATENT DOCUMENTS

| | | | |
|---|---|---|---|
| 2,255,090 A | 9/1941 | Tinker et al. | |
| 2,379,486 A | 7/1945 | Hill et al. | |
| 2,455,896 A | 12/1948 | Nagy et al. | |
| 2,684,924 A | 7/1954 | Rose et al. | |
| 4,567,174 A | 1/1986 | Edwards et al. | |
| 5,707,534 A | 1/1998 | Del Corral et al. | |
| 6,180,016 B1 | 1/2001 | Johnston et al. | |
| 6,187,192 B1 | 2/2001 | Johnston et al. | |
| 6,599,432 B2 | 7/2003 | Kross et al. | |
| 6,802,891 B2 | 10/2004 | Kritzler | |
| 6,833,075 B2 | 12/2004 | Hughes | |
| 6,861,002 B2 | 3/2005 | Hughes | |
| 6,878,285 B2 | 4/2005 | Hughes | |
| 6,955,761 B2 | 10/2005 | France et al. | |
| 6,957,743 B2 | 10/2005 | Johnston et al. | |
| 2002/0028754 A1 | 3/2002 | Johansen et al. | |
| 2003/0173287 A1 | 9/2003 | Johnston et al. | |
| 2003/0196955 A1 | 10/2003 | Hughes | |
| 2004/0149634 A1 | 8/2004 | Hughes | |
| 2004/0159605 A1 | 8/2004 | Hughes | |
| 2004/0200783 A1 | 10/2004 | Castellini | |
| 2004/0232068 A1 | 11/2004 | Johnston et al. | |
| 2005/0098495 A1 | 5/2005 | Hughes | |
| 2005/0235830 A1 | 10/2005 | Hughes | |
| 2005/0249791 A1 | 11/2005 | Hobbs et al. | |

FOREIGN PATENT DOCUMENTS

| | | |
|---|---|---|
| GB | 1095902 | 12/1967 |
| JP | 2942342 | 8/1999 |
| WO | WO 00/53150 | 9/2000 |

OTHER PUBLICATIONS

Slotta, et al., "Uber Biguanide, I.: Zur Konstitution der Schwermetall-Komplexverbindungen des Biguanids," *Berichte Der Deutschen Chemischen Gesellschaft* vol. 62, pp. 1390-1405 (Germany, 1929).
PCT/US2006/039218, International Search Report & Written Opinion.
Komorita, Takahashi et al., "Electronic Spectra of Square-Planar Bis (Biuretato) Cobalt (III)-Type Complexes", Bull. Chem. Soc. Jpn., 62:2163-2172 (1989).
Database Crossfire Beilstein, Beilstein Institut zur Forderung der Chemischen Wissenschaften, XP002452518, Database accession No. 1810543 (BRN) (1941).
Database Crossfire Beilstein, Beilstein Institut zur Forderung der Chemischen Wissenschaften, XP002452519, Database accession No. 2910745 (BRN) (1973).
Database Crossfire Beilstein, Beilstein Institut zur Forderung der Chemischen Wissenschaften, XP002452520, Database accession No. 1791070 (BRN) (1954).
Database Crossfire Beilstein, Beilstein Institut zur Forderung der Chemischen Wissenschaften, XP002452521, Database accession No. 1802577 (BRN) (1933).
Database Crossfire Beilstein, Beilstein Institut zur Forderung der Chemischen Wissenschaften, XP002452556, Database accession No. 121940 (BRN) (1989).

*Primary Examiner*—Humera N. Sheikh
*Assistant Examiner*—Hasan S Ahmed
(74) *Attorney, Agent, or Firm*—Sutherland Asbill & Brennan LLP

(57) ABSTRACT

Purification materials with broad spectrum antimicrobial properties and methods and devices for fluid treatment utilizing said materials are provided. The purification materials include biguanide hydrates and bases. A particular composition includes chlorhexidine dihydrate with the chemical formula ($C_{22}H_{30}N_{10}Cl_2 \cdot 1.3\ H_2O$), which is useful in water purification applications.

9 Claims, 11 Drawing Sheets

BROAD SPECTRUM ANTIMICROBIAL PURIFICATION MATERIALS AND METHODS FOR PURIFYING FLUIDS

CROSS-REFERENCE TO RELATED APPLICATION

This is application claims the benefit of U.S. Provisional Application No. 60/820,437, filed Jul. 26, 2006. The application is incorporated herein by reference in its entirety.

BACKGROUND OF THE INVENTION

This invention is generally in the field of antimicrobial materials useful in the purification of fluids, purification devices including antimicrobial materials, and methods of making and using such antimicrobial materials.

There is a general need for devices and methods to eliminate microorganisms from fluids for various applications, including the provision of safe or potable drinking water and breathable purified air. Many different methods are currently used for the purification of fluids. Representative examples include distillation, ion-exchange, chemical adsorption, filtering, and retention. Oftentimes, a number of different techniques must be combined to provide complete purification of fluids. These techniques can be costly, energy inefficient, and require significant technical expertise. Unfortunately, many low cost purification techniques do not adequately treat or remove harmful biological contaminants, bacteria, and viruses.

The Environmental Protection Agency (EPA) has set forth minimum standards for acceptance of a device proposed for use as a microbiological water filter. Common coliforms, represented by the bacteria *E. coli* and *Klebsiella terrigena*, must show a minimum 6-log reduction (99.9999% of organisms removed) from an influent concentration of $1 \times 10^7$ per 100 mL of water. Common viruses, represented by poliovirus 1 (LSc) and rotavirus (Wa or SA-11), which show a resistance to many treatment processes, must show a minimum 4-log reduction (99.99% of organisms removed), from an influent concentration of $1 \times 10^7$ per 100 mL of water. Cysts, such as those represented by *Giardia muris* or *Giardia lamblia*, are widespread, disease-inducing, and resistant to most forms of chemical disinfection. A device claiming cyst-removal must show a minimum 3-log reduction (99.9% of cysts removed) from an influent concentration of $1 \times 10^6$ per L or $1 \times 10^7$ per L.

It is known to use strong oxidants, such as phenols and hypochlorites, to effectively negate the potential threat of all microorganisms in water; however, these agents must be removed from water before consumption. Known biocompatible antimicrobial agents generally destroy only select microorganisms rather than a broad spectrum of microorganisms, thereby requiring the use of multiple biocompatible antimicrobial agents to effectively negate the potential threat of all microorganisms.

One conventional biocompatible antimicrobial agent is known as chlorhexidine. Chlorhexidine is a 1,6-di(4-chlorophenyl-diguanido) hexane having the chemical formula:

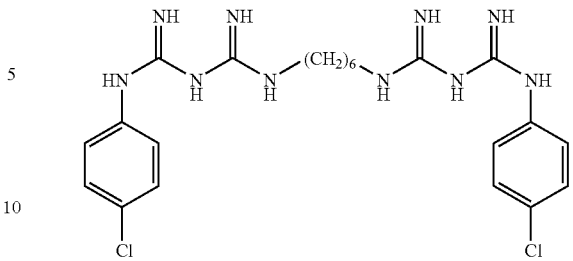

The IUPAC name for chlorhexidine is N,N"Bis(4-chlorophenyl)-3,12-diimino-2,4,11,13-tetrazatetradecanediimideamide. Chlorhexidine has a high level of antibacterial activity, low mammalian toxicity, and a strong affinity for binding to skin and mucous membranes. It has been used as a topical antiseptic for application to areas such as skin, wounds, and mucous membranes. Chlorhexidine also has been used as a pharmaceutical preservative and as a disinfectant for inanimate surfaces.

Historically, chlorhexidine has been used only in its salt soluble forms. Chlorhexidine salts, however, have an extremely bitter taste that must be masked in formulations intended for oral use. In addition, chlorhexidine salts are ineffective for applications requiring insoluble materials.

Chlorhexidine's antimicrobial activity is directed mainly toward vegetative gram-positive and gram-negative bacteria. It is ineffective against bacterial spores, except at elevated temperatures. Acid-fast bacilli are merely inhibited and not inactivated by aqueous solutions of chlorhexidine. At relatively low concentrations, chlorhexidine is bacteriostatic, while at higher concentrations, chlorhexidine is rapidly bactericidal. Chlorhexidine's fungicidal activity is subject to species variation. Although chlorhexidine and its know derivatives exhibit some antimicrobial activity, they unfortunately may not be effective against a broad spectrum of microorganism types.

Other water soluble antimicrobial chemical agents are known in the art. Representative examples of such conventional materials include soaps/detergents, surfactants, acids, alkalis, heavy metals, halogens, alcohols, phenols, oxidizing agents and alkylating agents. Most of these agents chemically alter (e.g., by an oxidation reaction, etc.) the cellular structure of microbes to inactivate them. These agents may have undesirable side-effects on the affected area of contamination (skin, clothes, paint, etc.) with often deleterious side-effects (discoloration and oxidation).

Accordingly, there remains a need for an inexpensive and biocompatible antimicrobial agent that will effectively inactivate a broad spectrum of microorganisms. There is also a need for a practical purification material comprising a biocompatible antimicrobial agent for purifying fluids. Desirably, the purification material would significantly exceed the minimum EPA requirements for designation as a microbial water purifier such that it is suitable for consumer and industry point-of-use applications.

SUMMARY OF THE INVENTION

A novel antimicrobial compound, purification materials, and methods are provided herein. In a particular embodiment, an antimicrobial material comprises a compound of the formula

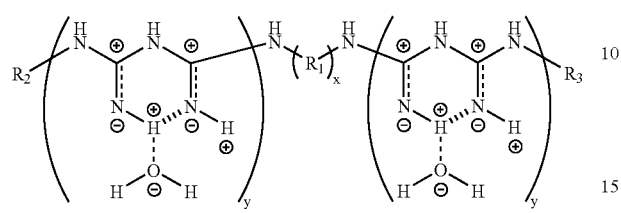

wherein $R_1$ comprises a straight chained, branched, or cyclic alkyl, alkenyl, alkynyl, or aryl group;

wherein $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a straight, chained, branched, or cyclic alkyl, alkenyl, alkynyl, aryl, heteroaryl, or heterocyclic group; and wherein x and y, independent of one another, are numbers between 1 and 3000.

In a particular embodiment, the antimicrobial material comprises chlorhexidine dihydrate, a compound of the formula

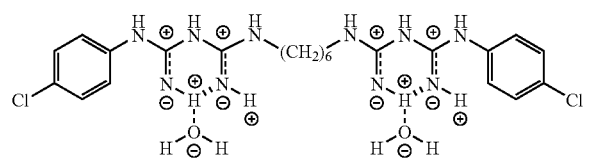

wherein $R_1$ is methyl, $R_2$ and $R_3$ are chloro-phenyl, x is 6, and y is 1.

In another particular embodiment, an antimicrobial material comprises a compound of the formula

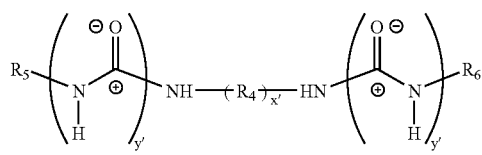

wherein $R_4$ comprises a straight chained, branched, or cyclic alkyl, alkenyl, alkynyl, or aryl group;

wherein $R_5$ and $R_6$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a straight chained, branched, or cyclic alkyl, alkenyl, alkynyl, aryl, heteroaryl, or heterocyclic group; and wherein x' and y', independent of one another, are numbers between 1 and 3000.

In a particular embodiment, the antimicrobial material comprises chlorhexidine base, a compound of the formula

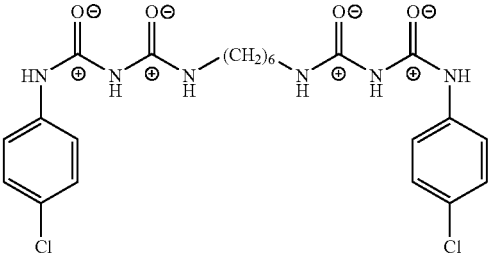

wherein $R_4$ is methyl, $R_5$ and $R_6$ are chloro-phenyl, x' is 6, and y' is 2.

In another aspect, methods are provided for making and using an antimicrobial material. In a particular embodiment, a method for inactivating microorganisms in a fluid is provided, comprising the steps of contacting a fluid in need of treatment with an antimicrobial material, wherein said contact is effective to inactivate at least one microorganism in the fluid. In particular embodiments, the fluid comprises water, a beverage, air, or a physiological fluid and the at least one microorganism comprises bacteria, fungi, virus, protozoa, or a combination thereof.

DETAILED DESCRIPTION OF THE INVENTION

Figure 1:
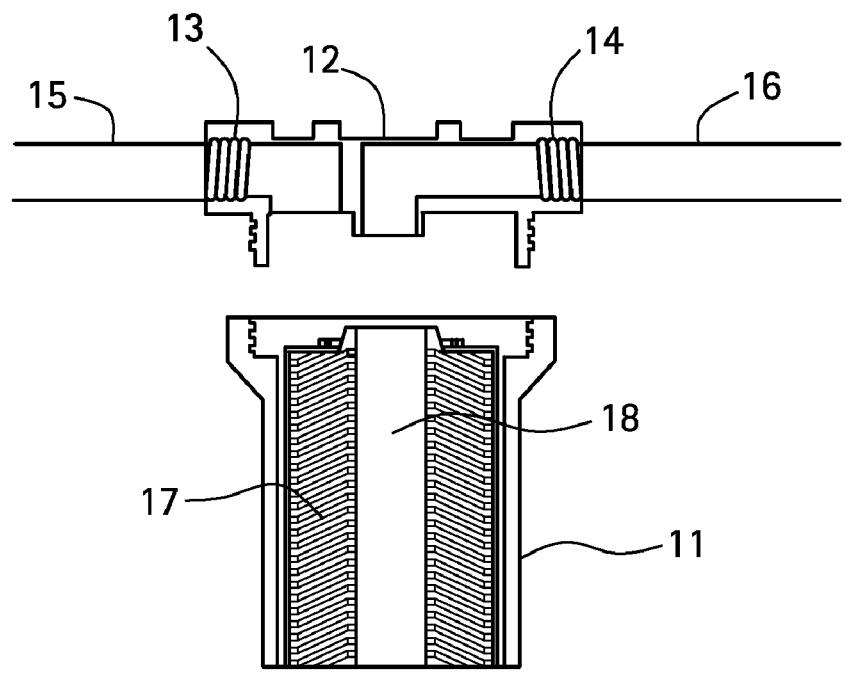
FIG. 1 is a cross-sectional view illustrating one embodiment of a filtration device containing a block filter which includes a purification material described herein.
Figure 2:
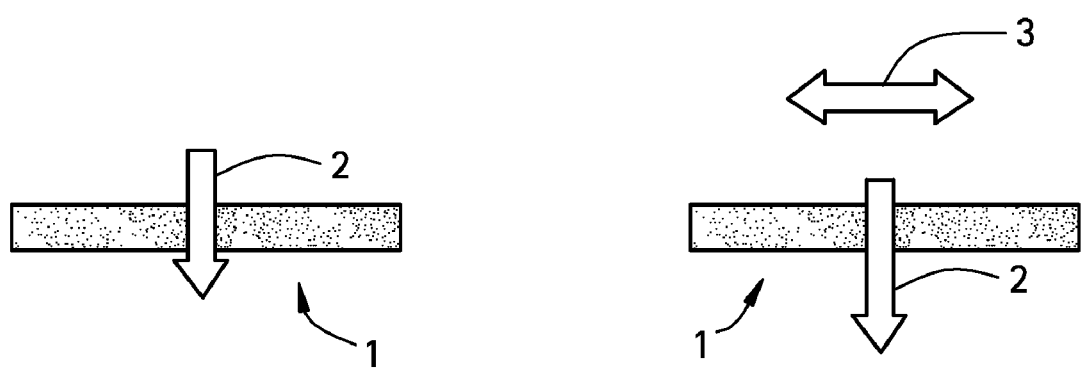
FIGS. 2A and 2B are schematic views of one embodiment of a purification material in the form of a sheet or film.
Figure 3:
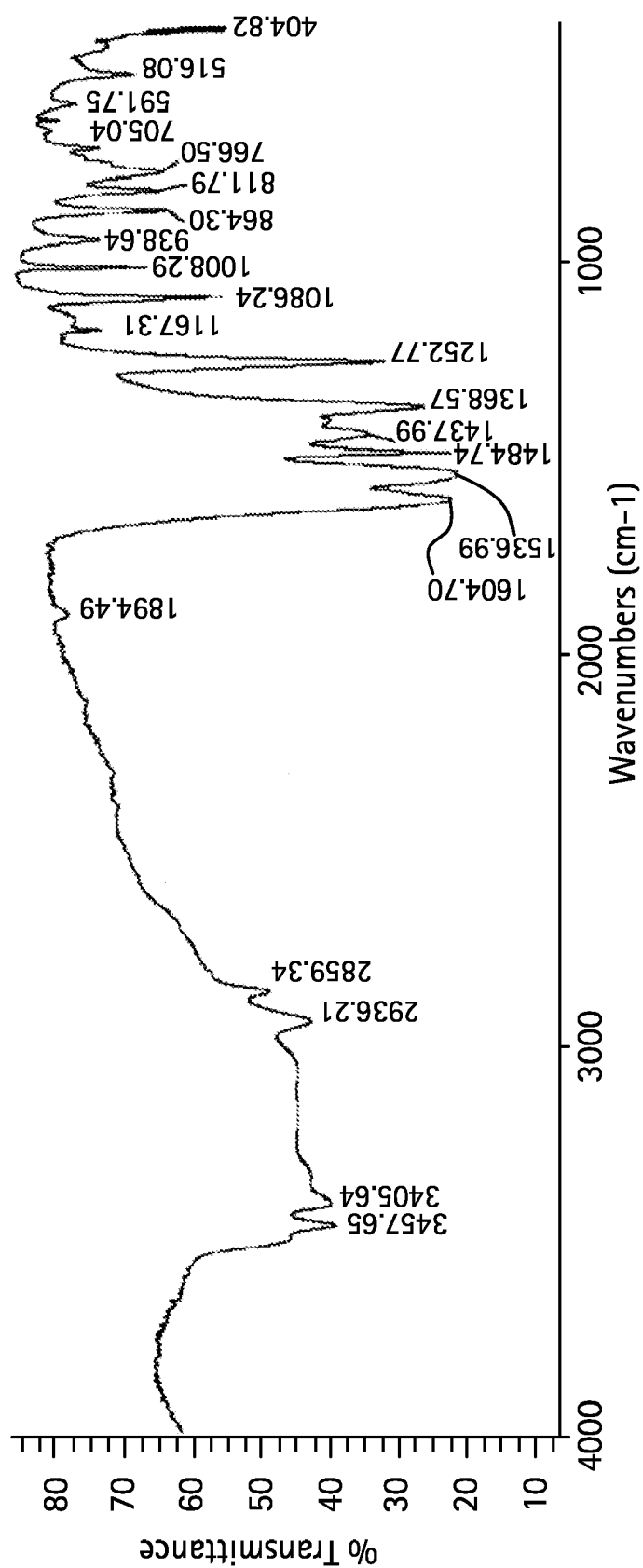
FIG. 3 is a FTIR spectrum of chlorhexidine dihydrate.
Figure 4:
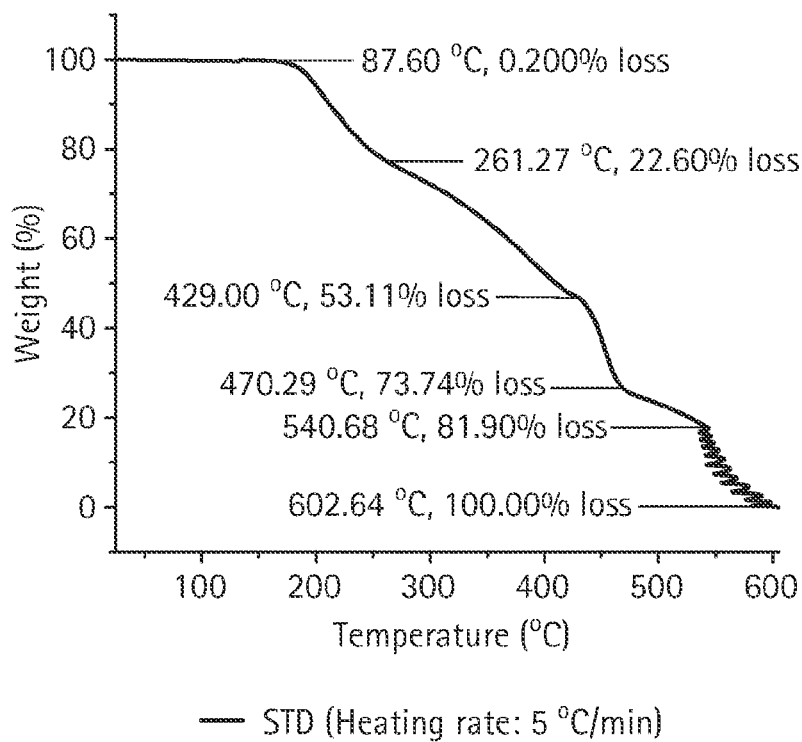
FIG. 4 is a TGA thermogram of chlorhexidine base.

Novel antimicrobial compounds have been discovered, and purification materials and methods have been developed therefrom. In one embodiment, the antimicrobial compound is produced by reacting a chlorhexidine compound (e.g., chlorhexidine diacetate) with sodium hydroxide (or another base) to form chlorhexidine dihydrate (actual: $C_{22}H_{30}N_{10}Cl_2 \cdot 1.3H_2O$; theoretical: $C_{22}H_{30}N_{10}Cl_2 \cdot 2H_2O$). Chlorhexidine dihydrate is an insoluble biguanide compound. It has an amorphous structure, which is in contrast to crystalline chlorhexidine base. Its surface energy is significantly less than many other materials, which beneficially allows water or another fluid to flow through it more easily than through other materials. Chlorhexidine dihydrate advantageously has a melting temperature far below its decomposition temperature, which allows it to be molded into different physical shapes without degrading the compound's chemical or structural integrity. Significantly, it has been found that chlorhexidine dihydrate has broad spectrum antimicrobial activity. Chlorhexidine dihydrate has been found to negate bacteria and many other kinds of microorganisms in an aqueous fluid.

The chlorhexidine dihydrate disrupts the microorganisms in a principally surface-dependent manner, advantageously without depleting the supply of the chlorhexidine dihydrate. That is, chlorhexidine dihydrate's antimicrobial functionality is effectively catalytic. The treatment is a zero-order reaction; no chlorhexidine dihydrate is consumed during treatment of a contaminated fluid. In contrast, the rate of reaction for chlorhexidine or its previously known conventional derivatives is second-order, as the reaction depends on both the concentration of chlorhexidine and the active sites of microorganisms. Conventional chlorhexidine is reacted and consumed. In contrast, chlorhexidine dihydrate is particularly suitable for use in purification/treatment devices and systems due to its insolubility, amorphous structure, low surface energy, catalytic nature, and broad spectrum antimicrobial activity. While not wishing to be bound by any theory, it is believed that other insoluble compounds that are of a cationic nature will exhibit a similar broad spectrum antimicrobial activity as the biguanide dihydrates and biguanide bases provided herein. In addition, it is believed that insoluble tri-guanide and tetra-guanide hydrates and bases or will exhibit similar broad spectrum antimicrobial activity using the same mechanism as the biguanide dihydrates and biguanide bases provided herein.

As used herein, the term "water insoluble" refers to substantial insolubility in aqueous fluids, particularly aqueous fluids having a pH in the range of about 3 to about 11, such as between about 4 and about 9, and particularly in the range of 6.0 to 8.0.

As used herein, the term "antimicrobial activity" refers to the property or capability of a material to inactivate microorganisms. Non-limiting examples of microorganisms include bacteria, fungi, and viruses. This "inactivation" renders the microorganism incapable of reproducing and therefore incapable of infecting other organisms and occurs by disruption of the bacteria, fungi or protozoa membrane, or by denaturization of the protein such as that which forms the protective capsid for viruses. As used herein, the term "broad spectrum antimicrobial activity" refers to the property or capability of a material to inactivate numerous different, or substantially all, types of microorganisms including bacteria (and its corresponding spores), fungi, protozoa and viruses. An antimicrobial agent that inactivates only a select group of microorganisms (e.g., either only gram positive cells or only gram negative cells) does not have broad spectrum antimicrobial activity.

The present purification compositions and treatment methods are not based on a chemically reactive agent. Rather, the present compositions and methods are based only on physical/mechanical contact between the purification material and the fluid to be treated. The microorganisms can be inactivated without separation from the fluid. That is, inactivation of the microorganisms is a physical phenomenon and need not (but optionally could) include removal of the skeletal remains of the inactivated microorganisms from the fluid, e.g., by filtration.

The Antimicrobial Compositions

The present antimicrobial compositions and devices may be further understood with reference to the following description and accompanying FIGS. 1-12. The compounds of the present purification materials generally include biguanide hydrates and biguanide bases having broad spectrum antimicrobial activity, as well as tautomers of the same. While not wishing to be bound by any theory, it is believed that the broad spectrum antimicrobial activity of the biguanide dihydrates and biguanide bases is due to the compounds' cationic nature. Generally, microorganisms have cell membranes composed of lipids and proteins. When the microorganisms are exposed to the biguanide dihydrates and biguanide bases, the microorganisms experience a change in surface charge in the cell membrane sufficient to disrupt the cell membrane and render the microorganisms incapable of reproduction.

In one embodiment, the composition includes a biguanide hydrate having the chemical formula (Formula I):

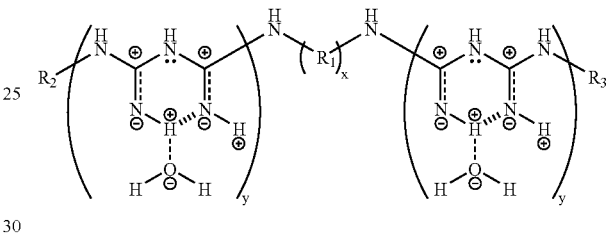

wherein $R_1$ comprises a straight chained, branched, or cyclic alkyl, alkenyl, alkynyl, or aryl group which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group; $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a straight chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group; and x and y, independent of each other, are numbers from 1 to 3000. in certain embodiments, y is a number from 1 to 4, and x is a number from 1 to 100, from 1 to 20, from 1 to 10, or from 1 to 8.

Once skilled in the art will appreciate that in selecting suitable or viable substitutions, the functional group should not eliminate or substantially impair the broad spectrum antimicrobial activity of the compound, and should not impair the chemical stability of the compound.

In one particular embodiment, the biguanide hydrate of Formula I comprises chlorhexidine dihydrate, having the chemical formula

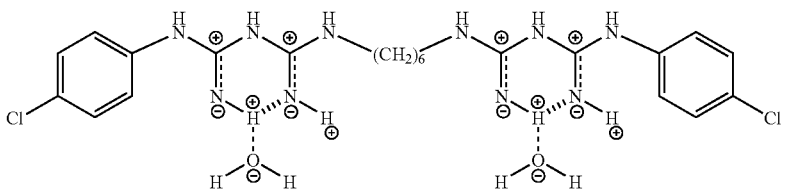

wherein $R_1$ is methyl, $R_2$ and $R_3$ are chloro-phenyl, x is 6, and y is 1.

In another embodiment of the biguanide hydrate of Formula I, $R_2$ and $R_3$, independent of one another, are electron-withdrawing groups.

In still other embodiments of the biguanide hydrate of Formula I, $R_2$ and $R_3$ are independently aryls, are independently substituted aryls, or are independently phenyls. In another embodiment of the biguanide hydrate of Formula I, $R_2$ and $R_3$ are independently substituted phenyls. The independently substituted phenyls may have ortho, para, or meta substitutions. The independently substituted phenyls may be identical to or different from one another.

In still another embodiment of the biguanide hydrate of Formula I, $R_2$ and $R_3$ are independently substituted halo phenyls. The independently substituted halo phenyls may have ortho, para, or meta substitutions. The independently substituted halo phenyls may be identical to or different from one another.

In various other examples of the biguanide hydrate of Formula I, $R_2$ and $R_3$ may independently be substituted halogens, substituted amines, substituted amides, substituted cyanos, or substituted nitros.

In another embodiment, the composition comprises a biguanide base having the chemical formula (Formula II):

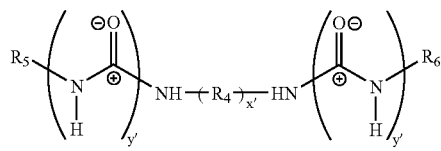

wherein $R_4$ comprises a straight chained, branched, or cyclic alkyl, alkenyl, alkynyl, or aryl group, which may be further substituted with a hydrogen, halogen, hydroxyl, amino, amido, alkylamino, arylamino, alkoxy, aryloxy, nitro, acyl, alkenyl, alkynyl, cyano, sulfo, sulfato mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a straight chained, branched, or cyclic alkyl, alkenyl, alkynyl, aryl, heteroaryl, or heterocyclic group, which may be further substituted with a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfa-moyl, phosphonyl, phosphinyl, phosphoryl, phosphino, thioester, thioether, anhydride, oximno, hydrazino, carbamyl, phosphonic acid, phosphonato, or any other viable functional group; and x' and y', independent of one another, are numbers from 1 to 3000. In certain embodiments, y' is a number from 1 to 4, and x' is a number from 1 to 100, from 1 to 20, from 1 to 10, or from 1 to 8.

In one particular embodiment, the biguanide base of Formula II comprises a chlorhexidine base having the chemical formula

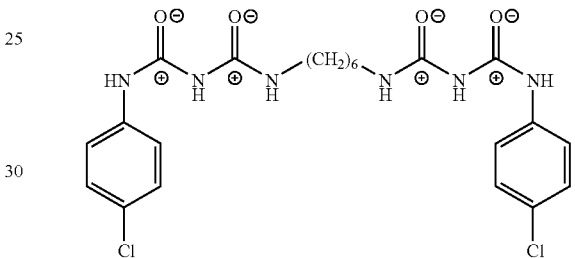

wherein $R_4$ is methyl, $R_5$ and $R_6$ are chloro-phenyl, x' is 6, and y' is 2.

In another embodiment of the biguanide hydrate of Formula II, $R_5$ and $R_6$ are independently electron-withdrawing groups.

In various other embodiments of the biguanide hydrate of Formula II, $R_5$ and $R_6$ are independently aryls, are independently substituted aryls, are independently phenyls. In one particular embodiment of the biguanide hydrate of Formula II, $R_5$ and $R_6$ are independently substituted phenyls. The independently substituted phenyls may have ortho, para, or meta substitutions. The independently substituted phenyls may be identical to or different from one another.

In another particular embodiment of the biguanide hydrate of Formula II, $R_5$ and $R_6$ are independently substituted halo phenyls. The independently substituted halo phenyls may have ortho, para, or meta substitutions. The independently substituted halo phenyls may be identical to or different from one another.

In various other examples of the biguanide hydrate of Formula II, $R_5$ and $R_6$ are independently substituted halogens, substituted amines, substituted amides, substituted cyanos, or substituted nitros.

The term "alkyl", as used herein, unless otherwise specified, refers to a saturated straight, branched, or cyclic, primary, secondary, or tertiary hydrocarbon of C1 to C20, and specifically includes methyl, ethyl, propyl, isopropyl, butyl, isobutyl, t-butyl, pentyl, isopentyl, neopentyl, hexyl, and isohexyl. The term includes both substituted and unsubstituted alkyl groups. Moieties with which the alkyl group can be substituted are selected from the group consisting of hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group.

The term "alkenyl", as referred to herein, and unless otherwise specified, refers to a straight, branched, or cyclic hydrocarbon of C2 to C10 with at least one double bond. The alkenyl groups can be optionally substituted in the same manner as described above for the alkyl group and can also be optionally substituted with a substituted or unsubstituted alkyl group.

The term "alkynyl", as used herein, and unless otherwise specified, refers to a C2 to C10 straight or branched hydrocarbon with at least one triple bond. The alkynyl groups can be optionally substituted in the same manner as described above for the alkyl groups and can also be optionally substituted with a substituted or unsubstituted alkyl group.

The term "aryl", as used herein, and unless otherwise specified, refers to any functional group or substituent derived from an aromatic ring. Non-limiting examples include phenyl, biphenyl, and napthyl. The term includes both substituted and unsubstituted moieties. The aryl group can be substituted with one or more moieties as described above for the alkyl groups or a substituted or unsubstituted alkyl group.

The term "heteroaryl" or "heteroaromatic", as used herein, refers to an aromatic or unsaturated cyclic moiety that includes at least one sulfur, oxygen, nitrogen, or phosphorus in the aromatic ring. Non-limiting examples are furyl, pyridyl, pyrimidyl, thienyl, isothiazolyl, imidazolyl, tetrazolyl, pyrazinyl, benofuranyl, benothiophenyl, quinolyl, isoquinolyl, benzothienyl, ixobenzofuryl, pyrazolyl, indolyl, isoindolyl, benimidazolyl, purinyl, carbazolyl, oxazolyl, thiazolyl, isothiazolyl, 1,2,4-thiadiazolyl, isoxazolyl, pyrolyl, quinazolinyl, pyridazinyl, pyrazinyl, cinnolyl, phthalazinyl, quinoxalinyl, xanthinyl, hypoxanthinyl, and pteridnyl. The heteroaryl or heteroaromatic group can optionally be substituted with one or moieties as described above for the alkyl group or a substituted or unsubstituted alkyl group.

The term "heterocyclic" refers to a saturated nonaromatic cyclic group which may be substituted, and wherein there is at least one heteroatom or non-carbon atom, such as oxygen, sulfur, nitrogen, or phosphorus in the ring. The heterocyclic group can be substituted in the same manner as described above for the heteroaryl group.

The term "aralkyl", as used herein, and unless otherwise specified, refers to an aryl group as defined above linked to the molecule through an alkyl group as defined above. The term alkaryl, as used herein, and unless otherwise specified, refers to an alkyl group as defined above linked to the molecule through an aryl group as defined above. The aralkyl or alkaryl group can be optionally substituted with one or more moieties selected from the group consisting of hydroxyl, carboxy, carboxamido, carboalkoxy, acyl, amino, halo, alkylamino, alkoxy, aryloxy, nitro, cyano, sulfo, sulfato, phospho, phosphato, or phosphonato.

The term "halo", as used herein, specifically includes chloro, bromo, iodo, and fluoro.

The term "alkoxy", as used herein, and unless otherwise specified, refers to a moiety of the structure —O-alkyl, wherein alkyl is as defined above.

The term "acyl", as used herein, refers to a group of the formula C(O)R', wherein R' is an alkyl, aryl, heteroaryl, heterocyclic, alkaryl or aralkyl group, or substituted alkyl, aryl, heteroaryl, heterocyclic, aralkyl or alkaryl, wherein these groups are as defined above.

Methods of Making the Compounds

The starting materials may be commercially available or may be synthesized or prepared according to methods known in the art. In one embodiment, the antimicrobial compound is made by reacting a biguanide compound (e.g., chlorhexidine diacetate in aqueous solution) with a base, such as sodium hydroxide. The biguanide compounds have the chemical formula (Formula III):

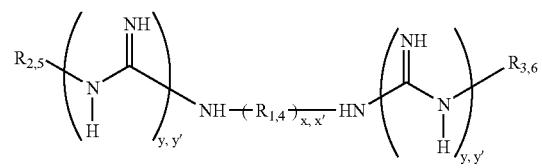

wherein $R_{1,4}$ comprises a straight, chained, branched, or cyclic alkyl, alkenyl, alkynyl, or aryl group which may be farther substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyt, phosphonyl, phosphinyl, phosphoryl, phosphino, thioester, thioether, anhydride, oximno, hydrazino, carbamyl, phosphonic acid, phosphonato, or any other viable functional group; $R_{2,5}$ and $R_{3,6}$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a straight, chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mereapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group; x (x') and y (y'), independent of each other, are numbers from 1 to 3000. In certain embodiments, y (y') is a number from 1 to 4, and x (x') is a number from 1 to 100, from 1 to 20, from 1 to 10, or from 1 to 8.

Where the biguanide compound has at least four carbon-nitrogen double bonds (e.g., y≧2), hydrogen bonding results in the formation of a heterocyclic structure having the chemical formula of Formula IV:

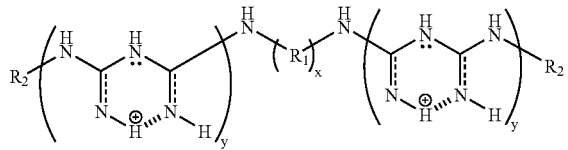

wherein $R_1$ comprises a straight, chained, branched, or cyclic alkyl, alkenyl, alkynyl, or aryl group which may be further substituted with any moieties such as hydrogen, halogen, hydroxyl, amino, amido, alkylarnino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group; $R_2$ and $R_3$, independent of one another, comprise a hydrogen, halogen, hydroxyl, amino, amido, alkylamino, arylamino, alkoxy, aryloxy, nitro, acyl, alkenyl, alkynyl, cyano, sulfo, sulfato, mercapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or a straight chained, branched, or cyclic alkyl, alkenyl, alkynyl, aryl, heteroaryl, or heterocyclic group, which may be further substituted with any moieties such as hydrogen, halogen, hydroxyl, amino, amido, alkylamino, arylamino, alkoxy, aryloxy, nitro, acyl, alkenyl, alkynyl, cyano, sulfo, sulfato, mereapto, imino, sulfonyl, sulfenyl, sulfinyl, sulfamoyl, phosphonyl, phosphinyl, phosphoryl, phosphino, thioester, thioether, anhydride, oximno, hydrazino, carbamyl, phosphonic acid, phosphonato, or any other viable functional group; x and y, independent of each other, are numbers from 1 to 3000.

While not wishing to be bound by any theory, it is believed that the reaction between the biguanide compounds and base involves two different reaction mechanisms, largely depending upon the pH of the reaction conditions. It is believed that under more basic conditions, the base reaction of the biguanide compound proceeds by the following mechanism to form a biguanide base.

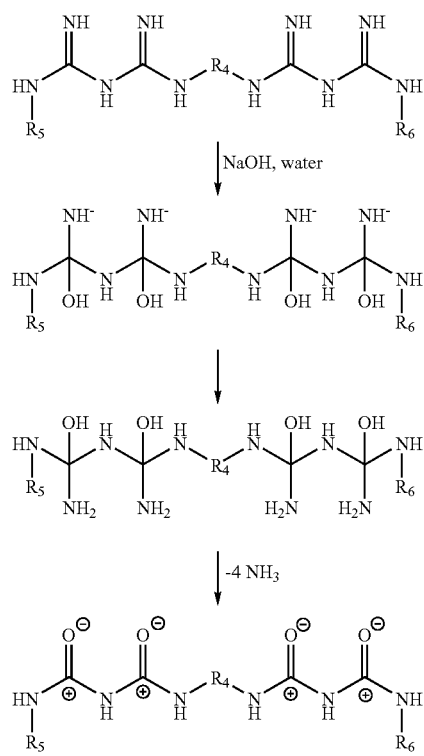

In the second reaction mechanism, it is believed that the biguanide compound (e.g., chlorhexidine diacetate) reacts with a dilute base to form a hydrated biguanide. Generally, hydrolysis of a biguanide would lead to the formation of ketone functionalities; however, elimination of the —$NH_2$ groups from the biguanide is either retarded or does not occur under mildly basic conditions, most likely due to strong intramolecular hydrogen bonding. Accordingly, it is believed that the soluble biguanide compound that undergoes hydrolysis has the above-described heterocyclic structure and forms a hydrated biguanide by the following mechanism.

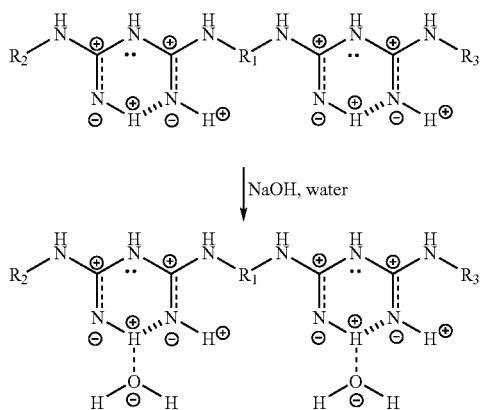

Of course, a reaction occurs with the solubilizing agent and the base (e.g., acetic acid) that made the chlorhexidine soluble such as chlorhexidine diacetate, chlorhexidine gluconate, or other soluble form of chlorhexidine).

Embodiments also include the compounds comprising the reaction intermediates of the foregoing chemical reactions.

Purification Materials and Devices

The antimicrobial compositions described here are provided in a form to contact a fluid in need of treatment. For example, the purification material or device may include one or more of the antimicrobial biguanide hydrates or biguanide bases, presented in a manner to facilitate contact with the fluid in need of treatment. In one embodiment, the purification material or device is designed to allow, or force, fluid flow through a porous structure that includes or consists of the antimicrobial composition.

The purification material may be in essentially any structure or form that provides sufficient contact with the fluid to be treated. For example, the structure may be in a loose granular or particulate form, or the structure may be in a unitary form in various geometric configurations, such as sheets, films, disks, rectangular blocks, closed cylinders, cylinders having one or more apertures (or bores) extending therethrough, and the like.

In one embodiment, the purification material is in the form a porous unitary structure. The structure can be made by compression molding a particulate form of the antimicrobial composition. The compression molding advantageously and desirably can be molded at ambient temperature conditions, that is, without input of heat. (Applying heat above the melting temperature would fuse the material into a perfectly continuous, consistent and nonporous structure.) The heatless pressure causes the particles to aggregate together, or fuse into a monolithic structure, with no loose particles while retaining its porosity. Desirably, the purification material has a melting temperature far below its decomposition temperature, allowing it to be molded into different physical shapes without jeopardizing the compound's chemical or structural integrity.

In one example, the structure of the purification material is a compression molded disk, and a purification device made from the disk further includes one or more layers of a porous support material disposed adjacent to one or both sides of the disk of antimicrobial material. For example, the porous support material may include a polymeric material attached to the disk to help maintain the structural integrity of the compression molded disk. In one case, the polymeric support material is a hydrophylic polypropylene (POREX™), and the disk of purification material is sandwiched between two layers of the porous hydrophylic polypropylene. In operation, fluid would flow through the support layers and through the disk of purification material.

Those familiar with the art of fluid treatment will understand that the pore size and physical dimensions of the purification material may be manipulated for different applications. In addition, changes in these variables will alter flow rates and back-pressure. Similarly, those skilled in the art will recognize that variations in the composition of the purification material will likewise effect the material properties of the purification material.

In still another embodiment, the present antimicrobial compositions may be coated on an inert carrier substrate. For example, the substrate could be in the form of glass or ceramic beads (e.g., spheres or other shapes) or other loose packing objects which increase the active/available surface area of the antimicrobial material.

This purification material or device may be used alone, or in combination with other materials and devices known in the art of fluid treatment. For instance, the purification material or device may be used in a process in series with a filtration device, for example as a pretreatment to remove larger-scale particulate matter and/or as a post treatment to filter out skeletal remains of inactivated microorganisms. As another example, the fluid may be treated using methods, materials, and systems known in the art to remove other organic or inorganic matter or solutes. Suitable filter media for pre-filtration are described for example in U.S. Pat. Nos. 6,187,192; 6,180,016; 6,957,743; 6,833,075; and 6,861,002; and in U.S. patent application Ser. Nos. 10/276,274 and 10/467,679.

One embodiment of a fluid treatment device comprising the present antimicrobial compositions in illustrated in FIG. 1. A housing 11 is mated with a cap 12 having an inflow orifice 13 and an outflow orifice 14. A water supply conduit is joined to the inflow orifice 13, to deliver non-treated water into the device, and a water discharge conduit 16 is joined to the outflow orifice 14, to conduct treated water from the device. Water passes into the housing 11 and is forced through the porous purification material 17, which is in the shape of hollow cylinder with an axial bore 18, by the pressure of the water flow. The treated water then passes into the axial bore 18 which connects to the outflow orifice 14.

FIGS. 2A-2B show two embodiments where the purification material described herein is in the form of a sheet or film. A purification material 1 can be used with normal flow-through of a fluid 2 through the purification material 1 (FIG. 2A). Alternatively, a purification material 1 can be used with cross-flow of a fluid 3 across the purification material 1 with fluid 2 flowing through the purification material 1 (FIG. 2B). The cross-flow fluid 3 sweeps across the surface of the purification material 1, which may decrease the level of particulate matter deposited thereon.

Applications of the Antimicrobial Materials

The compounds and treatment devices described herein have numerous possible applications. Advantageously, the treatment devices are of a nonsoluble and nonconsumable catalytic nature, and are capable of inactivating a broad spectrum of microorganisms. Generally, the compounds and purification materials can be used in applications where it is desirable to reduce and/or eliminate microorganisms in a fluid.

In a particular embodiment, the antimicrobial compounds embodied in the present invention are incorporated into treatment devices for water purification. Such treatment devices may be installed at the point of use. This may eliminate the need for chlorination of water supplies to protect against contamination of microorganisms.

In another embodiment, the purification material can be portable for obtaining potable drinking water at any time or place. These devices would be especially desirable in undeveloped third-world countries where one of the largest needs is potable drinking water.

The purification material and method are particularly useful in those applications where the required reduction in the concentration of microbiological contaminants significantly exceeds the EPA standards for microbiological water purification devices. In a particular embodiment of the invention, the purification material comprises a biguanide hydrate or biguanide base, described in detail herein. In the method corresponding to this particular embodiment, the microbiological contaminants are inactivated when the fluid is forced through the purification material by a difference in pressure on the influent and effluent sides or by a vacuum on the effluent side of the purification material.

In addition to functioning as a purifier for drinking water, the material of the present invention can also be used to purify water used for recreational purposes, such as water used in swimming pools, hot tubs, and spas, allowing the chlorine normally required to eliminate living microorganisms to be either reduced or completely eliminated.

Because the material of the invention efficiently inactivates microorganisms in aqueous solutions, it also has numerous applications in the pharmaceutical and medical fields. For example, the material of the invention can be used to inactivate microorganisms in physiological fluids or in devices, e.g., at-home dialysis machines.

In one particular embodiment, the present antimicrobial compositions and devices can be used for low-temperature sterilization techniques, eliminating the need for techniques requiring elevated temperatures and pressures, such as pasteurization. This would prove especially useful for both the food and beverage industries.

In another embodiment, the present antimicrobial compositions and devices can be used in hospital or industrial areas requiring highly purified air having extremely low amounts of microorganisms, e.g., intensive care wards, operating rooms, clean rooms used for care of immunosuppressed patients, or industrial clean rooms for manufacturing electronic and semiconductor equipment. The purification materials also can be used for residential air-purification. Such applications would be especially useful for individuals who suffer from heightened reactivity to air-borne microorganisms, such as fungi. In yet another embodiment, the purification material can may be used to protect individuals from air-borne microorganisms in the event of a bioterrorist attack.

In one particular application, the present antimicrobial compositions may be incorporated into a device designed to eliminate pathogenic protozoa (e.g., of the genus *Plasmodium* and phylum Apicomplexa) that cause diseases such as malaria. Malaria is typically transmitted to humans through mosquitoes and remains a leading cause of death in undeveloped countries. Mosquitoes are infected with the protozoa from water reservoirs and lakes where the mosquitoes breed. Eliminating the protozoa from the breeding habitats of the mosquitoes could virtually eliminate outbreaks of malaria.

Numerous other applications exist for which the present antimicrobial compositions and purification materials can be used. Representative examples include the treatment of water used in cooling systems, fermentation applications and cell culture, and inactivation of microorganisms in gases (e.g., anesthetics, carbon dioxide used in carbonated beverages, gases used to purge process equipment, etc.).

In each of these applications, the method of using the present antimicrobial compositions and purification materials is relatively simple: The fluid to be treated is brought into physical contact with the antimicrobial compositions. Typically, the fluid will be forced from one side of the porous purification material through to the other side of the purification material due to a pressure drop across the purification material. The pressure driven flow can be conducted using conventional fluid pumps or gravity fed.

The devices, systems, and methods described above will be further understood with reference to the following non-limiting examples.

EXAMPLE 1

Elemental Analysis of Chlorhexidine Hydrate

Chlorhexidine ($C_{22}H_{30}N_{10}Cl_2$), obtained commercially, was reacted with sodium hydroxide to form chlorhexidine dihydrate ($C_{22}H_{30}N_{10}Cl_2 \cdot 3H_2O$). Approximately 100 g of a starting material chlorhexidine diacetate was dissolved in 1300 mL of warm deionized water at approximately 50° C. 6 M potassium hydroxide (KOH) was added drop-wise with stirring. A precipitate formed immediately and continued to form upon addition of base until the solution reached a pH of 11. The precipitate was filtered and washed six times with warm, 50° C., deionized water, and then dried in an oven at 60° C. to produce approximately 78 g of chlorhexidine dihydrate. These compounds were analyzed using energy dispersive x-ray spectroscopy (EDX), Fourier transform infrared spectroscopy (FTIR), thermogravimetric analysis (TGA), and proton nuclear magnetic resonance ($^1$H NMR),

EDX

Chlorhexidine and chlorhexidine dihydrate were analyzed using EDX, a technique well known to those of skill in the art. Table 1 provides both the theoretical and actual elemental composition of chlorhexidine and chlorhexidine dihydrate obtained from the EDX analysis.

TABLE 1

Theoretical and actual elemental compositions

| Element | Chlorhexidine | | Chlorhexidine dihydrate | |
|---|---|---|---|---|
| | Theoretical | Actual | Theoretical | Actual |
| C | 52.28% | 52.14% | 49.77% | 50.32% |
| H | 5.98% | 5.90% | 6.57% | 6.25% |
| N | 27.27% | 27.36% | 26.39% | 26.49% |
| Cl | 14.03% | 14.15% | 13.35% | 12.96% |
| O | — | — | 3.92% | 3.98% |

FTIR

FTIR was used to compare the characteristic peaks of different functional groups in chlorhexidine dihydrate and chlorhexidine. Chlorhexidine had peaks at 3513, 3473, 3410, 3371 cm$^{-1}$, characteristic of N—H stretching, and peaks at 1635 and 1595 cm$^{-1}$, characteristic of aromatic and aliphatic guanidine absorptions (ArNHC(=N—H)NHAr) and ((CH$_3$)$_2$ NC(=N—H)C(CH$_3$)$_2$). The chlorhexidine dihydrate spectrum of FIG. 3 had peaks at 3458 and 3406 cm$^{-1}$, characteristic of N—H stretching. The decreased frequencies likely were attributable to hydrogen bonding. The chlorhexidine dihydrate spectrum also had a broad band between 3300-2850 cm$^{-1}$ that was characteristic of an intermolecular OH hydrogen-bonded bridge (typically appearing between 3405 and 2936 cm$^{-1}$). Chlorhexidine dihydrate also had the aromatic guanadine peak at 1605 cm$^{-1}$. The decreased frequency, again, likely was attributable to hydrogen bonding.

TGA

Figure 5:
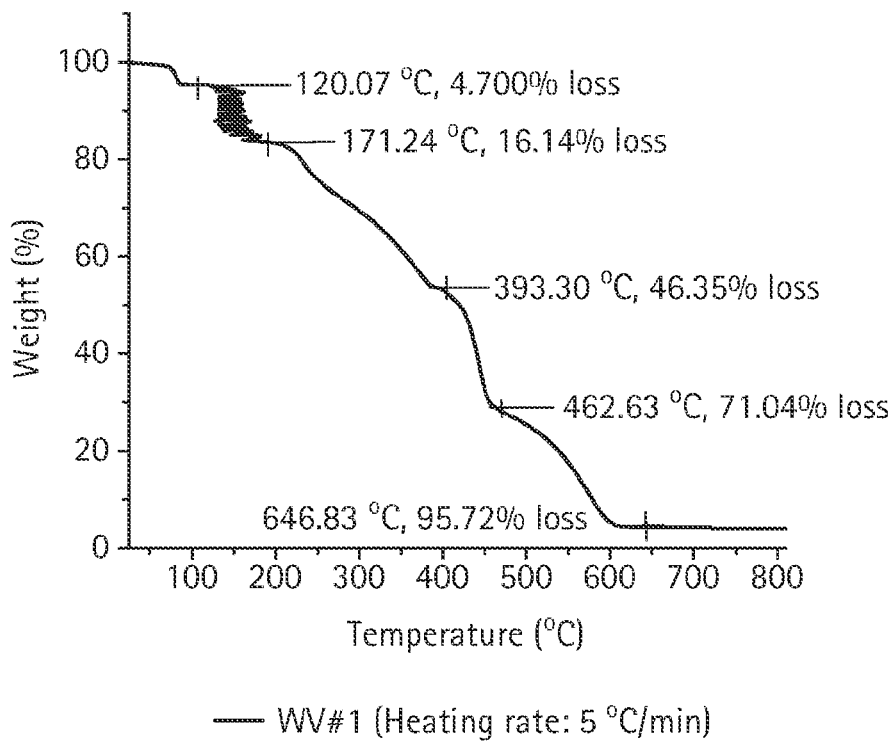
FIG. 5 is a TGA thermogram of chlorhexidine dihydrate.
Figure 6A:
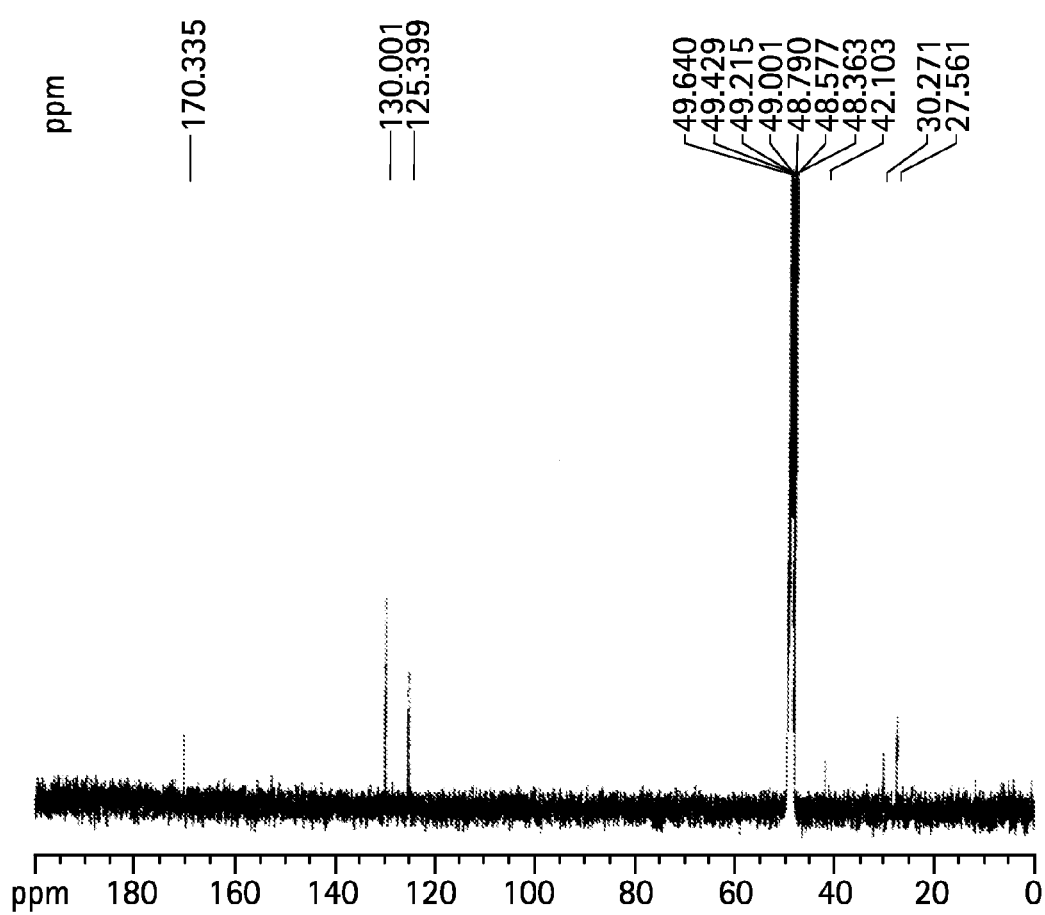
FIGS. 6A and 6B are $^1$H NMR plots of chlorhexidine.
Figure 6B:
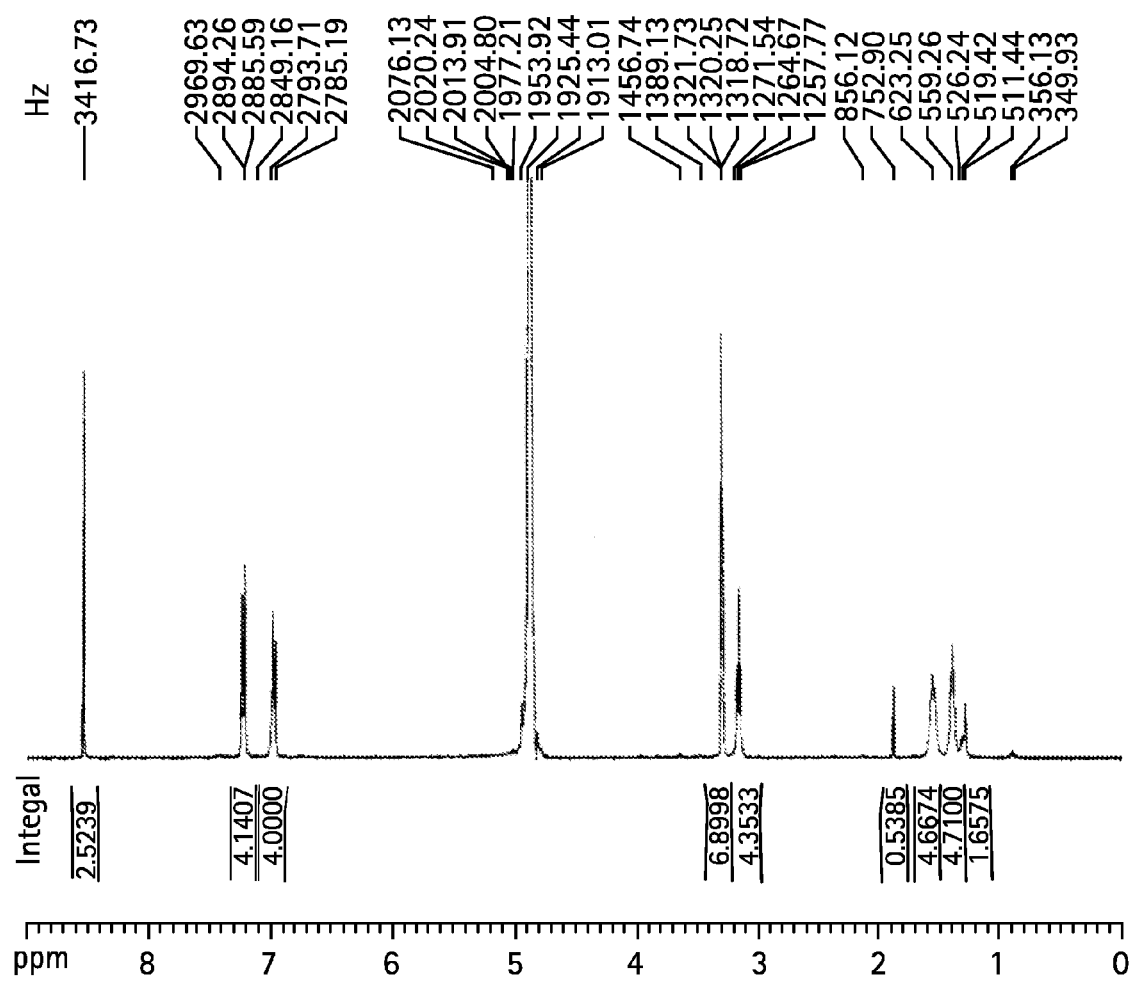
Figure 7A:
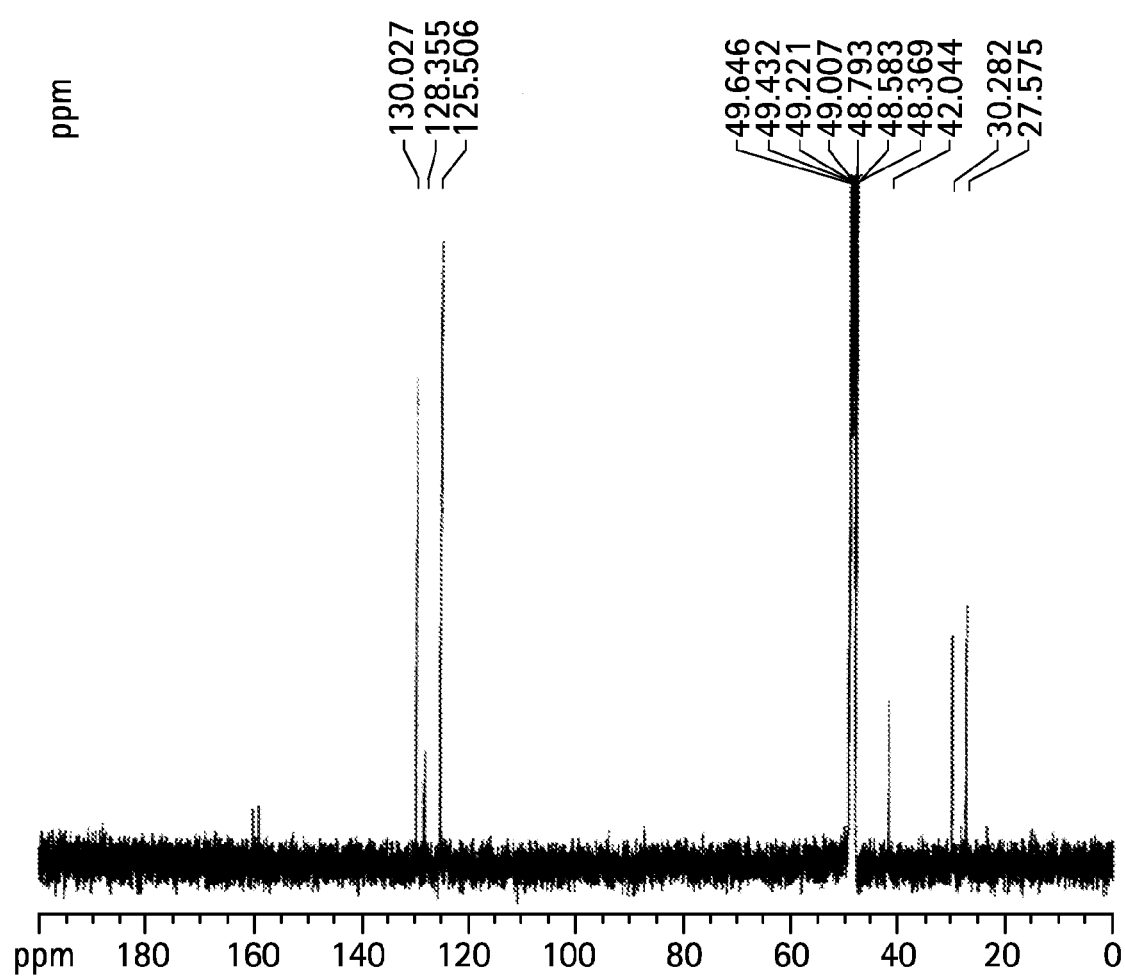
FIGS. 7A and 7B are $^1$H NMR plots of chlorhexidine dihydrate.
Figure 7B:
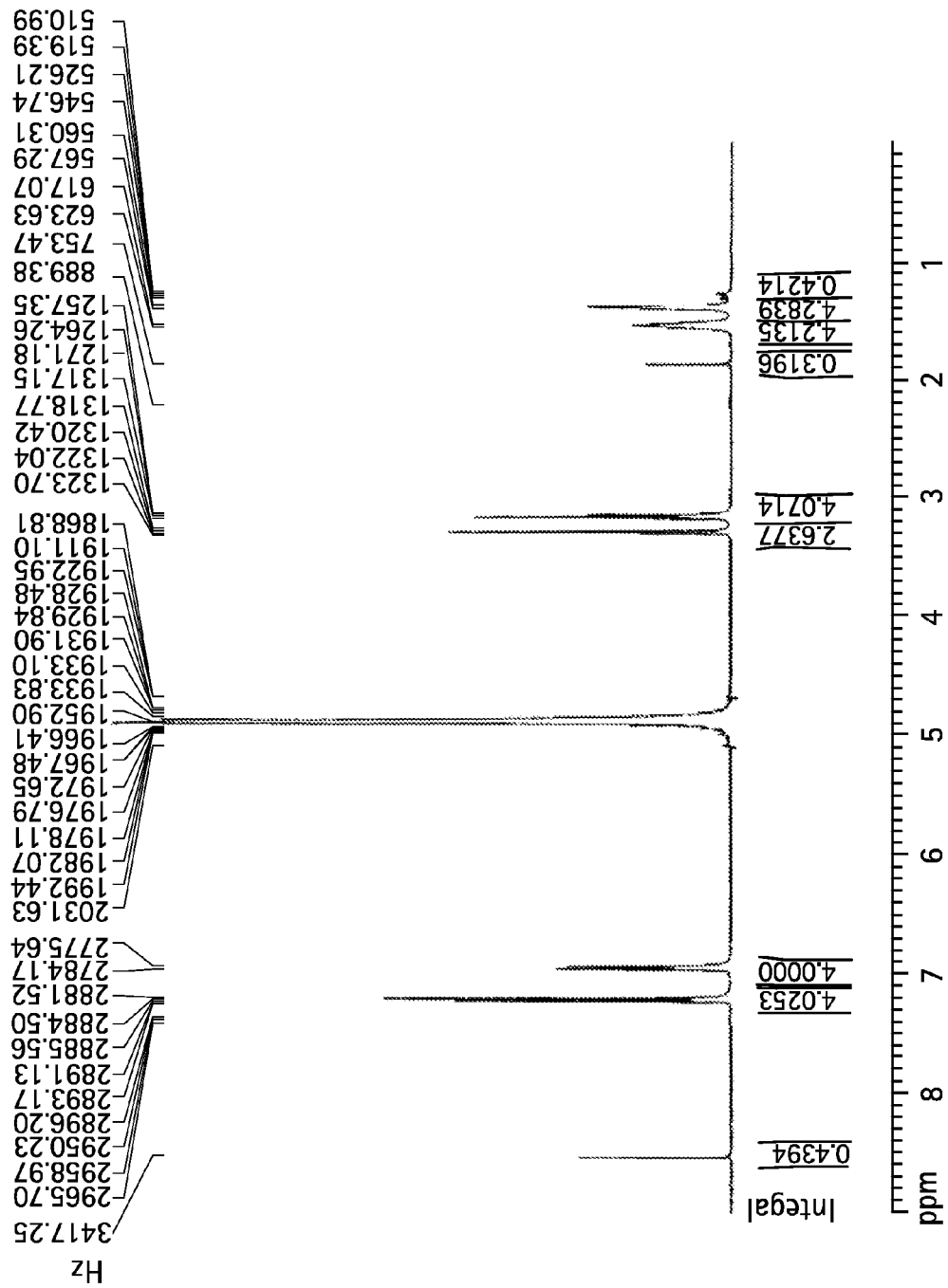
Figure 8:
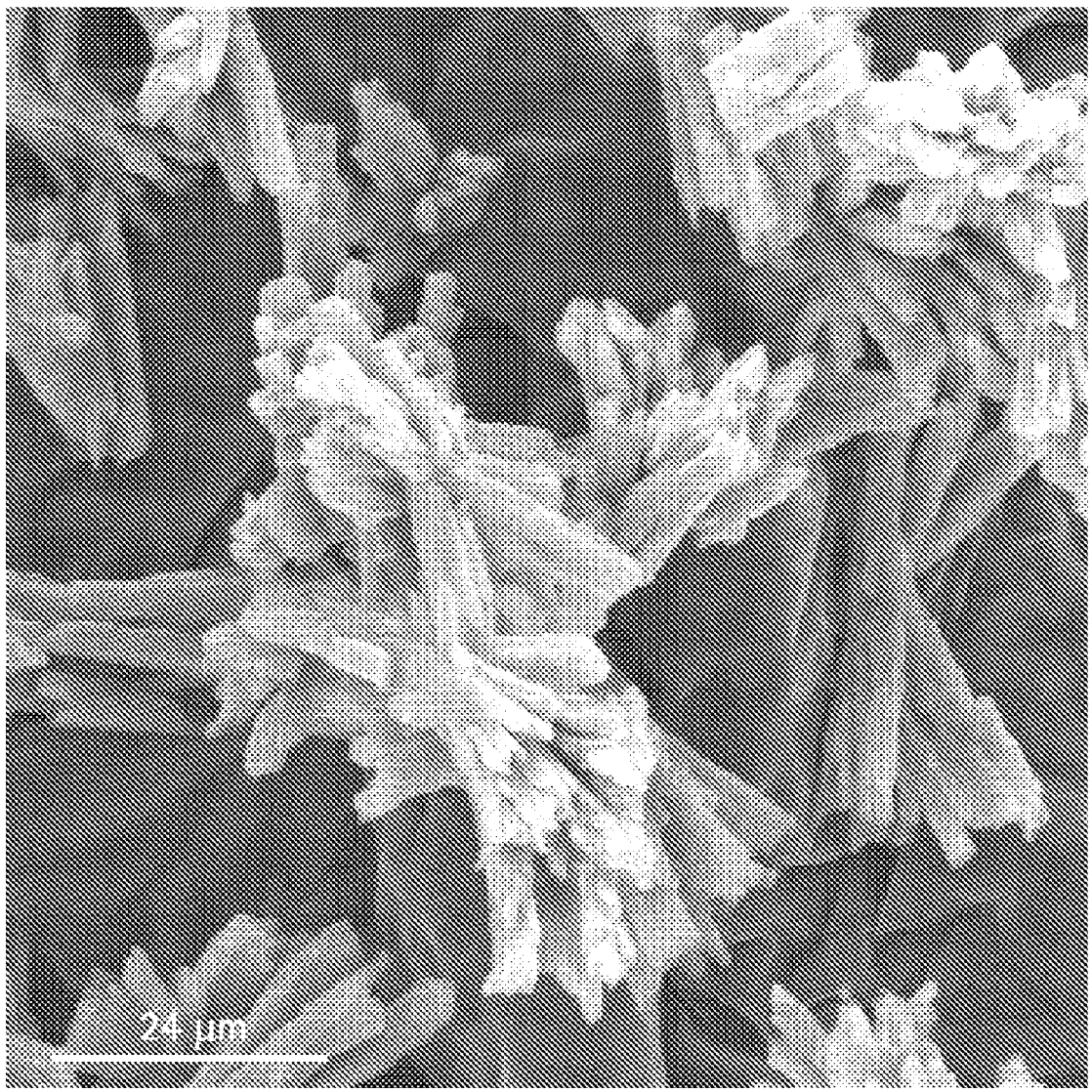
FIG. 8 is a SEM image of 1000 magnification of chlorhexidine.
Figure 9:
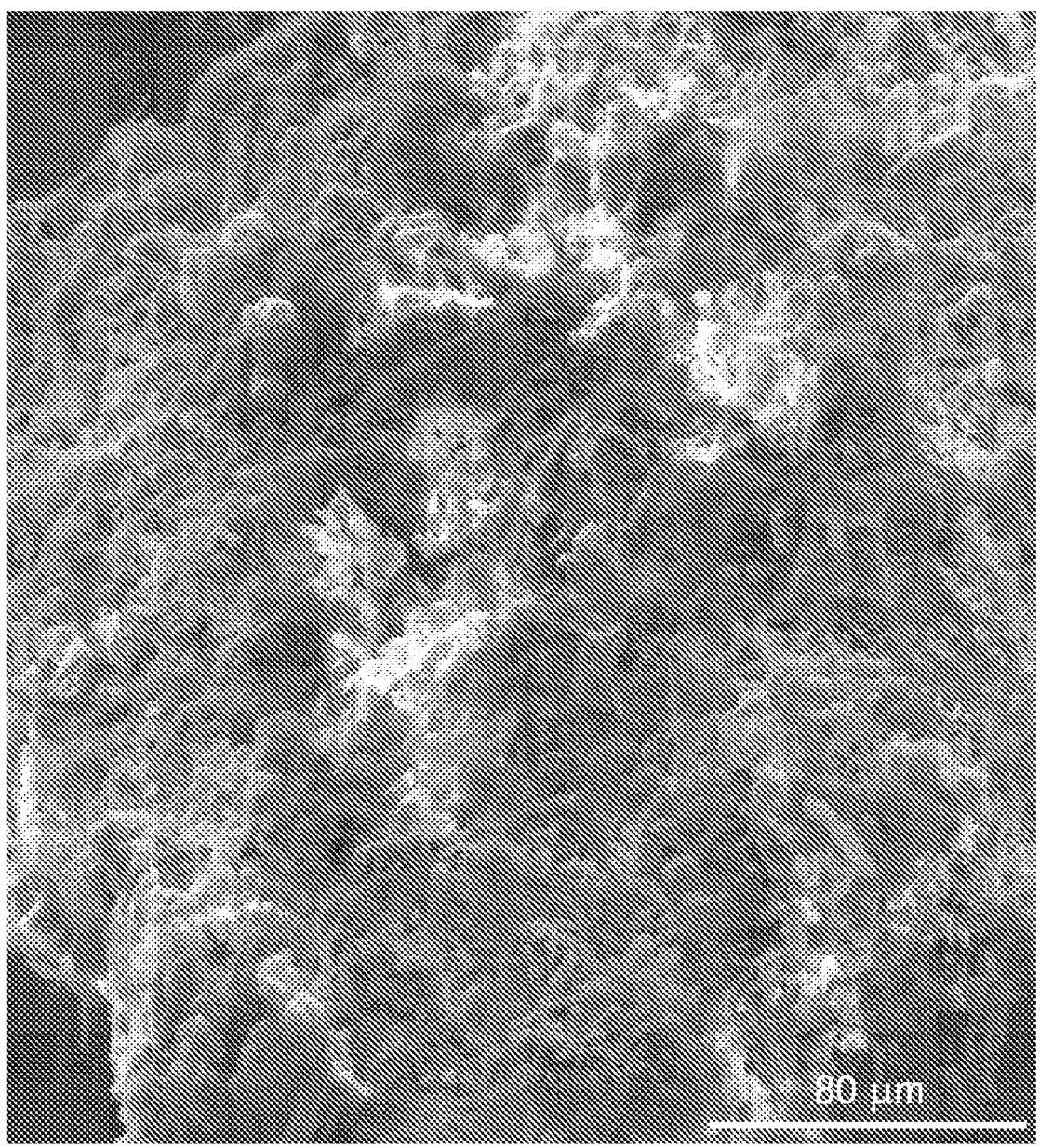
FIG. 9 is a SEM image of 1000 magnification of chlorhexidine dihydrate.
Figure 10:
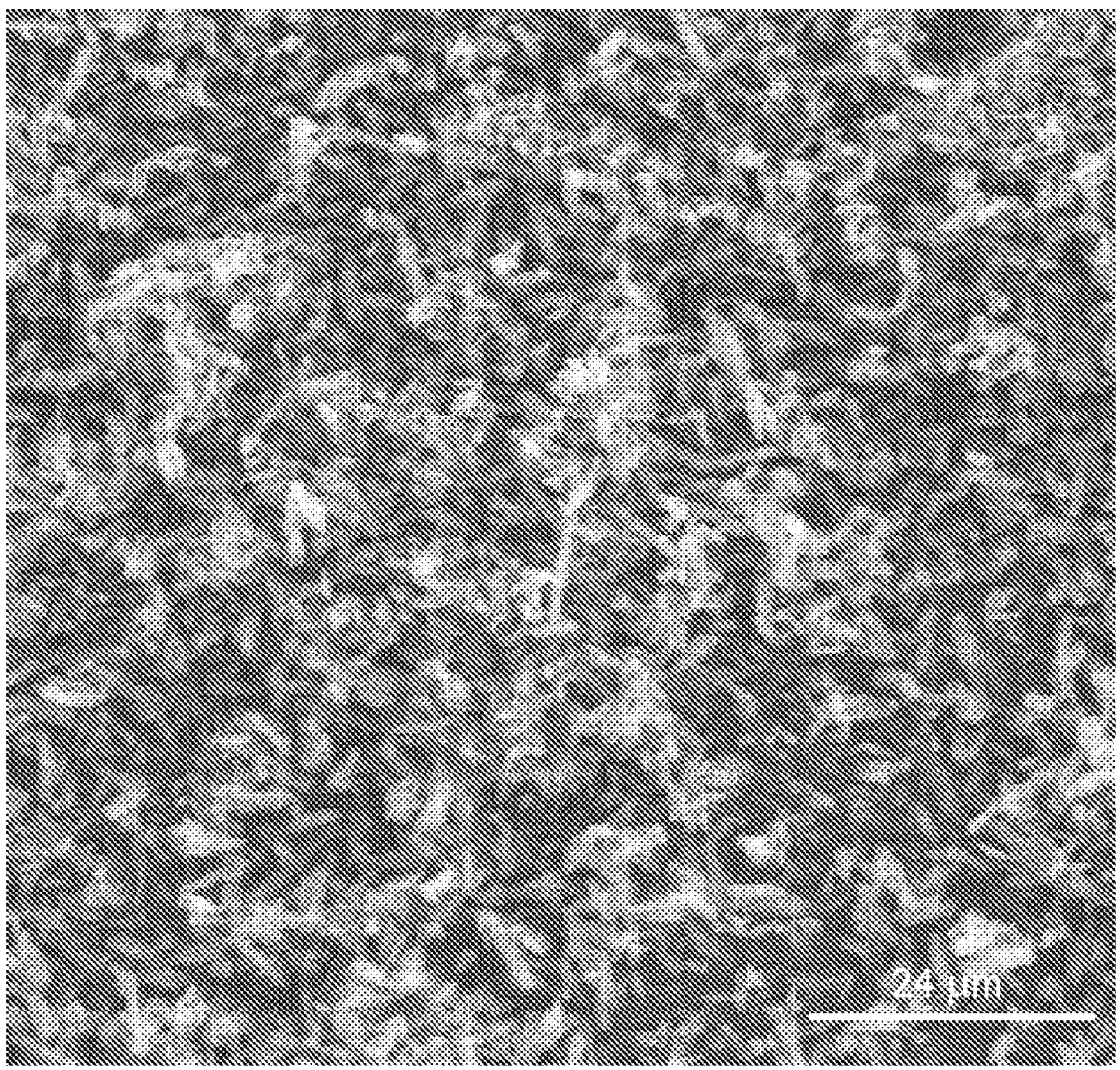
FIG. 10 is a SEM image of 1000 magnification of chlorhexidine dihydrochloride.

TGA was used to determine the moisture content of chlorhexidine base (FIG. 4) and chlorhexidine dihydrate (FIG. 5). As shown by the derivative weight loss curve of FIG. 5, there was a loss of a small molecule (presumably water) at 100° C. and a mass decrease of 4.700% at 120.07° C. for chlorhexidine dihydrate. The mass loss likely corresponded to the 3.98% oxygen from the EDX analysis which equates to 4.5 wt. % water present in the chlorhexidine dihydrate.

$^1$H NMR

Proton nuclear magnetic resonance ($^1$H NMR) spectroscopy was used to analyze the structure of chlorhexidine dihydrate. The $^1$H NMR spectrum of chlorhexidine (FIG. 6) had peaks at 8.5, 7.25, 7.0, 3.3, 3.15, 1.9, 1.6, 1.4, and 1.25 ppm. The $^1$H NMR spectrum of chlorhexidine dihydrate (FIG. 7) had peaks at 8.5, 7.2, 6.9, 3.3, 3.15, 1.85, 1.6, 1.35, and 1.25 ppm, similar to that of chlorhexidine. The intensities, however, were different. Specifically, the peak at 8.5 ppm was significantly less intense in the chlorhexidine dihydrate spectrum. The peaks at 8.5, 1.85, and 1.35 ppm showed no spin-spin coupling and were therefore in rapid equilibrium in the deuterated methanol solvent (tautomerization). The water appeared to preferentially stabilize some of the tautomers of chlorhexidine.

EXAMPLE 2

Structural Analysis of Chlorhexidine and its Derivatives

Scanning electron microscope (SEM) images were taken of chlorhexidine (FIG. 8), chlorhexidine dihydrate (FIG. 9), and chlorhexidine hydrochloride (FIG. 10) using techniques well known to those skilled in the art.

A loose porous granular form of the chlorhexidine dihydrate had a particle size range of 3 to 180 µm and a mean particle diameter of 35.35 µm, as measured using a Beckman-Coulter LS Particle Size Analyzer. In contrast, the chlorhexidine had a very narrow particle size range. The broad particle range of chlorhexidine dihydrate is due to the significant amorphous and semicrystalline fractions of the mass, whereas pure chlorhexidine is 100% crystalline.

A block of the same material was subjected to pressure to partially fuse the particles into a continuous block with no loose particles, but remained porous. It typically would be undesirable to heat the material above its melting temperature because the particles would fuse completely into a continuous and nonporous block of material, drastically reducing the surface area of the material available for contacting a fluid to be treated.

The morphology of chlorhexidine dihydrate and chlorhexidine were evaluated using X-Ray Diffraction spectroscopy.

EXAMPLE 3

Porosity and Bulk Density of Chlorhexidine Dihydrate Chlorhexidine, and Chlorhexidine Hydrochloride The material properties of chlorhexidine dihydrate, chlorhexidine, and chlorhexidine hydrochloride were analyzed to compare their dry bulk density and porosity to water.

Bulk Density

The materials were loosely packed into tared 50 ml graduated cylinders and agitated with a vortex mixer to further pack the materials in the cylinders. The weight of the material was determined and then divided by the volume of material to determine the bulk density. The calculated bulk densities are shown in Table 2. The larger value for the dihydrate is due to the significant amorphous fraction of the material that is not present in the pure chlorhexidine. The amorphous particles are smaller than crystals and fill the voids between crystals, allowing for a greater packing density of particles.

TABLE 2

Bulk density of chlorhexidine and its derivatives

| Material | Bulk Density (g/cc) |
| --- | --- |
| Chlorhexidine dihydrate | 0.70 |
| Chlorhexidine | 0.64 |
| Chlorhexidine hydrochloride | 0.15 |

Porosity

To measure the porosity of the materials to water, samples were placed in a ¾" inner diameter plastic tube fitted with a plug with a hole in the middle. A wire mesh, on top of the plug, prevented the powder from passing through the plug. Deionized water was passed through the sample until the material was sufficiently packed and a second wire mesh was positioned on top of the sample. Water was added to the tube to a height of 25 centimeters above the plug of material. This height was maintained to plus or minus one cm in order to maintain a constant pressure. The porosity was calculated by calculating the volumetric flow rate (volume/time), multiplying by the cross-sectional area (2.775 cm$^2$), and dividing by the thickness. Accordingly, the rate should increase proportionally with increases in the cross section and decreases in the thickness. The plug thickness, volume of water, time, and porosity are shown in Table 3.

TABLE 3

Porosity of chlorhexidine and its derivatives

| Sample | Thickness (cm) | Volume of water (mL) | Time (min) | Porosity (mL cm$^2$/min/cm) |
| --- | --- | --- | --- | --- |
| Chlorhexidine dihydrate | 1.9 | 79.0 | 15.25 | 7.55 |
| Chlorhexidine | 1.1 | 27.5 | 19.25 | 3.60 |

Chlorhexidine hydrochloride was not able to be tested because of the small particulate size.

EXAMPLE 4

Characterization of Chlorhexidine and Chlorhexidine Dihydrate

Chlorhexidine and chlorhexidine dihydrate were evaluated to characterize the phase transitions and to determine the melting points, density, solubility, and surface energy of the materials. Chlorhexidine was obtained commercially and chlorhexidine dihydrate was prepared as in Example 1.

DSC

Figure 11:
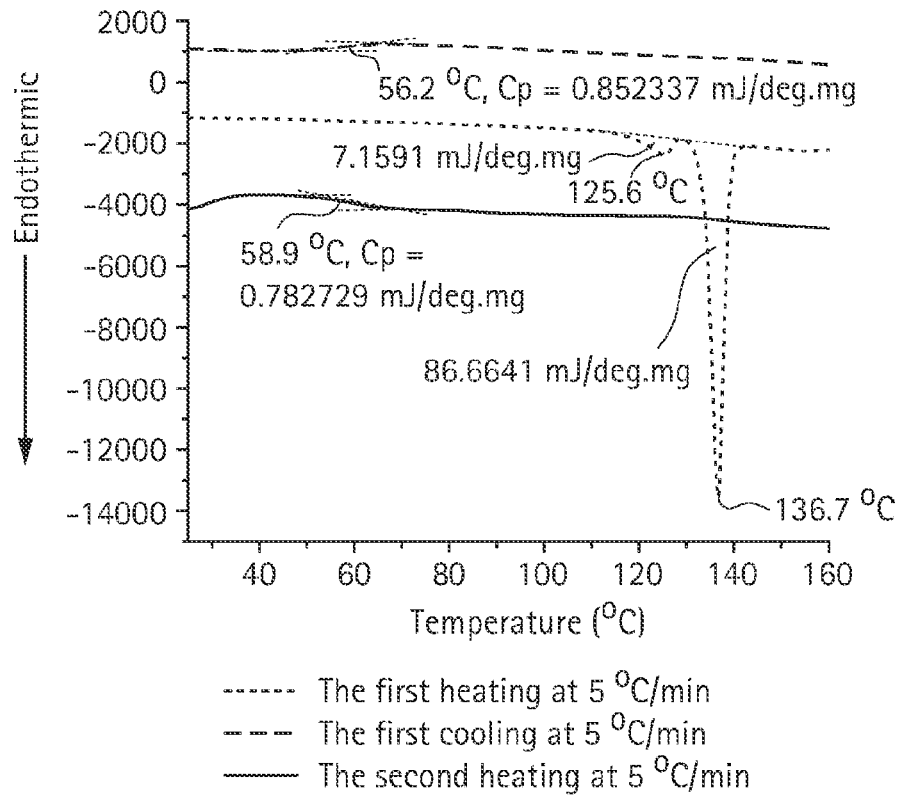
FIG. 11 is a DSC thermogram of chlorhexidine base.
Figure 12:
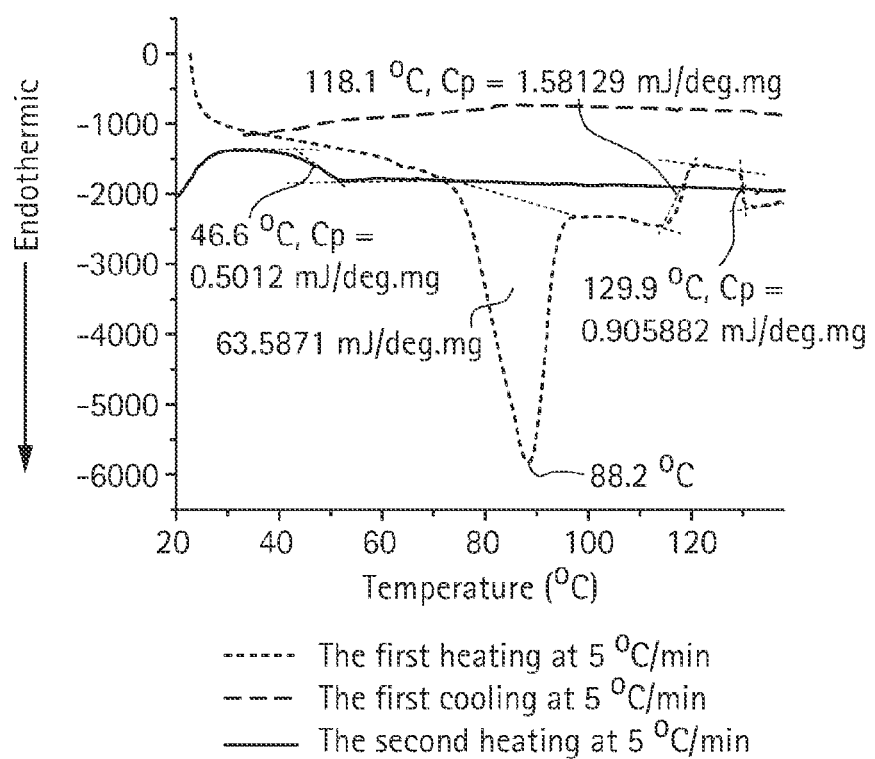
FIG. 12 is a DSC thermogram of chlorhexidine dihydrate.

Differential scanning calorimetry (DSC) was used to characterize the phase transitions of chlorhexidine base and chlorhexidine dihydrate. The DSC curves of chlorhexidine base and chlorhexidine dihydrate are illustrated in FIGS. 11 and 12, respectively.

Melting Point

The melting point was taken using a Melt-Temp apparatus (Laboratory Instruments Inc.). Chlorhexidine dihydrate melted at a temperature in the range of about 80° C. to about 86° C., consistent with the DSC analysis. Upon recrystallization of the chlorhexidine dihydrate (using a solubizing mixture of chloroform and methanol, filtration, and drying of the chlorhexidine dihydrate in a dessicator under vacuum), the chlorhexidine dihydrate melted at temperature in the range of about 131° C. to about 133° C., indicating that the amorphous fraction had been removed and the compound dehydrate to essentially the neat form of chlorhexidine. The melting point of chlorhexidine was at a temperature in the range of about 133° C. to about 136° C.

Density

Chlorhexidine and chlorhexidine dihydrate were melted on a glass slide heated on a hot plate. These glassy materials easily fractured into large chunks. One of these chunks from each sample was used to determine the density of the material. Using a binary solvent system consisting of chlorobenzene (density=1.102 g/cc) and carbon tetrachloride (density=1.492 g/cc), the chunk of material was suspended. The solution was adjusted until the particle remained hovering in mid solution without floating to the surface or sinking to the bottom. The resulting solution was weighed in a 10 mL volumetric flask and the density was calculated. The procedure was repeated at least 4 times for each sample. The densities are shown in Table 4.

TABLE 4

Density of chlorhexidine and chlorhexidine dihydrate

| | Density (g/cc) |
| --- | --- |
| Chlorhexidine dihydrate | 1.266 ± .001 |
| Chlorhexidine | 1.270 ± .001 |

Solubility

A sample of material was placed in a small vial with a few mL of solvent. The solution was stirred by shaking for several hours and then allowed to sit for a week equilibrating.

A 1 mL aliquot drawn from the solution using an Eppendorf pipette was placed in a weigh boat and dried in an oven. The dried sample was weighed. Measurements of the alcohol and water solvents were taken after three hours of mixing and again after a week. At the three hour measurement, it was necessary to centrifuge the sample in order to separate the solvent solution from the particulate matter. The solubilities are shown in Table 5.

TABLE 5

Solubility of chlorhexidine dihydrate

| Solvent | Chlorhexidine Dihydrate Solubility (mg/mL) | |
| --- | --- | --- |
| Water | <0.5 (3 days) | <0.4 (7 days) |
| Methanol | 3.6 (3 days) | 2.8 (7 days) |
| Ethanol | 1.7 (3 days) | 0.6 (7 days) |
| Iso-propanol | 0.9 (3 days) | 0.4 (7 days) |
| MIBK | 21.1 (7 days) | |
| Chloroform | 5.6 (7 days) | |
| Methylene Chloride | 5.6 (7 days) | |
| Ethyl Acetate | 10.0 (7 days) | |

Note that the reduction in solubility of chlorhexidine dihydrate in water is likely due to dissolution without agitation and chlorhexidine dihydrate's natural tendency to be insoluble in water. For comparison, the solubility of chlorhexidine base is reported to be 0.0008% (Block, S. S. *Disinfection, Sterilization, and Preservation*, Lippincott, Williams and Wilkins, New York, 2001) and 0.08% (Merck Index).

The effect of temperature on the solubility of chlorhexidine dihydrate in water was determined by placing a sample of chlorhexidine dihydrate in a 100 mL round bottom flask with 50 mL of deionized water. The round bottom flask contained a stir bar and was placed in an oil bath on a hot plate. The solution was gradually warmed. Aliquots were taken every 15° C. The aliquot was taken from the solution using of a syringe fitted with a micropore filter (Whatman fiberglass filter GF/D, pore size 2.7). The filter separated the solution from the suspended material. The solution was dried in a weigh boat at 60° C. overnight. The temperature dependence of solubility is shown in Table 6.

TABLE 6

Temperature dependence of chlorhexidine dihydrate solubility in water

| Temperature (° C.) | Solubility (mg/mL) |
|---|---|
| 30 | 0.46 |
| 45 | 0.74 |
| 60 | 0.78 |
| 75 | 0.92 |
| 90 | 0.89 |

The material had very limited solubility in both hot and cold water; however, chlorhexidine dihydrate had appreciable solubility in hot methanol, chloroform, methylene chloride, and ketones.

Surface Energy

Glass slides were cleaned in hot chromic acid, deionized water and blown dry. Two slides were treated with hexamethyldisilazane to lower their surface energy. Solutions of chlorhexidine dihydrate in chloroform/methanol and chlorhexidine in methylene chloride/methanol were prepared. The slides were coated using a dip-coater with a dipping speed of 2.8 mm/min. The HMDS treated slides produced very poorly coated films, indicating that the surface energy is high for these organic materials since the surface energy of HMDS slides is approximately 25 dyne cm. The untreated slides produced very uniform thin films. The mean contact angles are shown in Table 7.

TABLE 7

Surface energy of chlorhexidine and chlorhexidine dihydrate

| | Mean Contact Angle (S.D.) | |
|---|---|---|
| Solution | Chlorhexidine dihydrate | Chlorhexidine |
| Water (72.2 dyne/cm) | 7.08 (0.26) | 10.28 (0.38) |
| Water/Ethanol (90:10, 51.3 dyne/cm) | 13.08 (0.48) | 15.3 (0.53) |

TABLE 7-continued

Surface energy of chlorhexidine and chlorhexidine dihydrate

| | Mean Contact Angle (S.D.) | |
|---|---|---|
| Solution | Chlorhexidine dihydrate | Chlorhexidine |
| Water/Ethanol (70:30, 36.1 dyne/cm) | 18.44 (1.7) | 13.5 (7.3) |
| Water/Ethanol (50:50, 30.0 dyne/cm) | 0 | 0 |

The contact angles for pure water were consistent with a material with a relatively high surface energy for an organic material. The inability to cast a film on HMDS treated glass slides confirmed this. However, the trend of the contact angles was a typical for most materials. Typically, angles decrease with increased concentration of ethanol because the ethanol lowers the surface tension of the testing solution. There appeared to be some sort of chemical interaction that was affecting the surface energy measurement. When ethanol was added to a small amount of chlorhexidine dihydrate, the material greatly increased in volume without going into solution. Similar forces may have been at play with these materials, affecting the contact angle measurement.

EXAMPLE 5

Antimicrobial Activity of Chlorhexidine Dihydrate

Columns having a length of 30.48 cm and diameter of 0.75 in were packed with particle beds comprising chlorhexidine dihydrate having lengths of 19 cm, 2.5 cm, and 4.1 cm. A 40 mL mixture of inocculum (comprising 35 million *B. subtilis*, 91 million *E. coli*, 130 million *R. terrigena*, and 100 million *A. niger*) and water was passed by gravity through the chlorhexidine dihydrate particle bed. The treated water showed significant reductions in contaminants, as shown in Table 8.

TABLE 8

Reduction of bacterial growth using chlorhexidine dihydrate

| Organism | Inoculum | Effluent (1.9 cm) | % Reduction | Effluent (2.5 cm) | % Reduction | Effluent (4.1 cm) | % Reduction |
|---|---|---|---|---|---|---|---|
| *B. subtilis* | $35 \times 10^6$ | <1000 | >99.997 | $14 \times 10^5$ | 99.6 | <1000 | >99.997 |
| *E. coli* | $91 \times 10^6$ | <1000 | >99.999 | <1000 | >99.999 | <1000 | >99.999 |
| *R. terrigena* | $130 \times 10^6$ | <1000 | >99.999 | <1000 | >99.999 | <1000 | >99.999 |
| *A. niger* | $100 \times 10^6$ | <1000 | >99.9 | 8000 | 99.2 | <1000 | >99.9 |
| Flow Time | | 1.0 hour | | 2.0 minutes | | 1.5 hours | |

EXAMPLE 6

Antimicrobial Activity of Chlorhexidine Base

A 40 mL mixture of inocculum comprising 6.4 million *E. coli* and water was passed by gravity flow through a chlorhexidine base particle bed. It took 54 minutes for the fluid to pass through the particle bed. The treated fluid showed a greater than 99.999% reduction in *E. coli*.

EXAMPLE 7

Antimicrobial activity of Chlorhexidine Dihydrate Under Pumped Fluid Flow Conditions Dechlorinated city of Atlanta tap water was inoculated with a culture of *E. coli* bacteria and pumped through a 0.25 inch chlorhexidine dihydrate treatment device at a rate of 1 to 2 L/min up to 80 L. Bacterial recovery was determined by Aerobic Plate Count and is shown in Table 9.

TABLE 9

Reduction of bacterial growth using chlorhexidine dihydrate

| Volume of treated inoculated water run through device (L) | Total Aerobic Plate Count (# colonies/mL) |
| --- | --- |
| Untreated Sample | $8.6 \times 10^8$ |
| 20 | 10 |
| 40 | <10 |
| 60 | <10 |
| 80 | <10 |

EXAMPLE 8

Changes in Organics and Halides from Chlorhexidine Dihydrate

Water contaminated with *E. coli* ($10^{11}$ colony units) was treated with a chlorhexidine dihydrate (6.35 mm thickness) filled cell. The water before and after treatment was collected and analyzed to determine the total organic content (TOC) of the water samples. In addition, the water was analyzed for additive materials that may have emanated from the treatment cartridge containing chlorhexidine dihydrate. As shown in Table 10, the amount of total organic materials did not vary significantly and the total organic halides vary very slightly with the volume of contaminated water flowed through the device. The total halides (TOX) values were very small. It is possible that even these small values were the result of insufficient filtering by the porous ceramic filters in the cartridge that prevent the chlorhexidine dihydrate particulate material from entering the fluid stream.

TABLE 10

TOC and TOX for water treated with chlorhexidine hydrate

| Sample, Total Liters | Analysis | Run 1 mg/mL | Run 2 mg/mL |
| --- | --- | --- | --- |
| 0 L | TOC | 27 | |
| | TOX | <2 | <2 |
| 20 L | TOC | 36 | |
| | TOX | 2.6 | 2.7 |
| 40 L | TOC | 27 | |
| | TOX | <2 | 2.6 |
| 60 L | TOC | 23 | |
| | TOX | 3.2 | <2 |
| 80 L | TOC | 20 | |
| | TOX | 3.2 | <2 |

EXAMPLE 9

Chemical Kinetics of Chlorhexidine Dihydrate

The composition of chlorhexidine dehydrate produced mortality in all microorganisms with a minimum or greater mean 10-log reduction upon treatment of an influent contaminated water stream with a particle bed of insoluble chlorhexidine dihydrate. While it is known that soluble chlorhexidine salts are bactericidal for some microorganisms, the purification materials embodied herein require insoluble antimicrobial agents. Thus, the previously known chlorhexidine salts are unacceptable for use in the purification materials embodied herein.

The chlorhexidine dihydrate reaction mechanism is zero-order. A zero-order reaction is independent of material concentrations. The reaction rate can be described mathematically by the equations $$-R_A = \frac{dC_A}{dt} = k$$

$$C_{Ao} - C_A = C_{Ao} - X_A = kt$$

$$\text{for } t = \frac{C_{Ao}}{k}$$

where $C_A$ is concentration of material A, $C_{Ao}$ is the initial concentration of material A, t is time and k is the reaction constant. Generally, reactions are zero-order only in certain concentration ranges—for example at high concentrations of chlorhexidine dihydrate; however, no concentration of chlorhexidine dihydrate has been identified as being of a non-zero order reaction. The chlorhexidine dihydrate reaction rate appears to be limited only by the surface area, as described by the following expression $$-\frac{1}{\text{surface area}} \frac{dN_A}{dt} = k$$

wherein $N_A$ is the number of moles N of material A. The equation is based on the assumption that a given thickness dimension (dz) of the material remains constant, derived from the following series of calculations.

$C = N/V$ $dC/dt = d(N/V)/dt$ $V = \text{Surface Area} * \text{thickness}(dz)$ $1/SA * dN/dt = k * dz$ The results of the examples are consistent with this belief—no chlorhexidine dihydrate was consumed during dynamic testing of *E. coli* colonized in water flowed at a rate of 1 to 2 L/min. up to a total of 80 L through a 0.25 inch thickness disc of chlorhexidine dihydrate which resulted in a 100% inactivation of *E. coli*, as described in Example 6. Accordingly, the reaction of chlorhexidine dihydrate appears to be of a "catalytic" nature. Conversely, typical applications involving soluble chlorhexidine gluconate result in its consumption and approach a second-order reaction. The same is true for most other known antimicrobial agents. Thus, chlorhexidine dihydrate is particularly suitable for use as a purification material.

Although the antimicrobial activity of chlorhexidine dihydrate is zero-order, the reaction rate may be increased by increasing the collisions between the reaction molecules (chlorhexidine hydrate and the microorganisms). The "collision factor" ($Z_{AB}$) between two reactants (A and B) is described by the simplified equation $$Z_{AB} = \frac{\text{number of collisions of } A \text{ with } B}{\text{sec. cm}^3}$$

If $Z_{AB}$ is increased by a reaction condition, pressure for example, then the overall reaction will proceed faster. More specifically, if water containing microorganisms is forced under pressure to flow through a particle bed of chlorhexidine dihydrate, the collision frequency between the microorganisms and the chlorhexidine dihydrate surface will increase, thereby increasing the overall rate of inactivation of the microorganisms. The biochemical kinetics involving microorganisms are essentially the same as surface driven reactions, wherein the rate constant increases with increases in the collision frequency.

Although a reaction may be zero-order, the total rate of flow of a contaminated fluid through a device will reach a point of diminishing returns when the contact (residence) time becomes a factor. At this flow rate, the rate of reaction becomes time dependent and is described by the following expression $$R = k_t C_A$$

It is noted that studies to date have identified no point wherein the contact time becomes a rate-limiting factor for chlorhexidine dihydrate.

Publications cited herein and the materials for which they are cited are specifically incorporated herein by reference. Modifications and variations of the methods and devices described herein will be obvious to those skilled in the art from the foregoing detailed description. Such modifications and variations are intended to come within the scope of the appended claims.

We claim:

1. An antimicrobial material comprising a biguanide hydrate mixture which comprises a compound of the formula

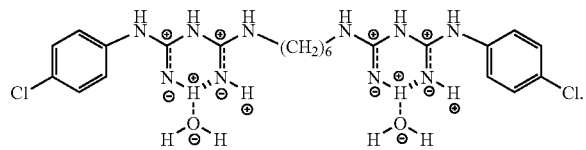

2. An antimicrobial material comprising a biguanide hydrate mixture which comprises a compound of the formula

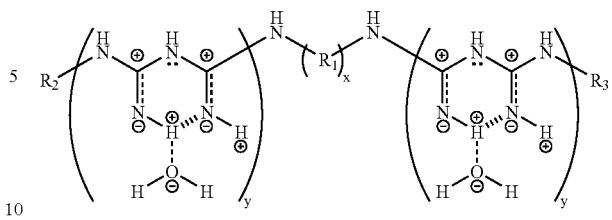

wherein $R_1$ is methylene;
wherein $R_2$ and $R_3$, independent of one another, comprise a halo-substituted phenyl; and
wherein x is a number from 1 to 6 and y is 1
wherein the solid biguanide hydrate mixture is produced by a process which comprises hydrolysis of a water soluble biguanide compound with a dilute aqueous base.

3. An antimicrobial material comprising a biguanide hydrate mixture, which is in the form of $C_{22}H_{30}N_{10}Cl_2 \cdot 1.3H_2O$, which comprises a compound of the formula

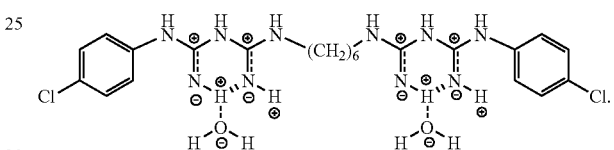

4. The material of claim 2, wherein the halo-substituted phenyl is a fluoro-substituted phenyl.

5. The material of claim 2, wherein x is 6.

6. The material of claim 4, wherein x is 6.

7. The material of claim 2, which is in the form a porous unitary structure.

8. The material of claim 4, which is in the form a porous unitary structure.

9. The material of claim 2, wherein the hydrolysis of the water soluble biguanide compound with a dilute aqueous base comprises dissolving the biguanide compound in water at approximately 50° C. and adding a potassium hydroxide solution to the biguanide solution.

* * * * *